United States Patent
Mousa et al.

(10) Patent No.: US 11,178,923 B1
(45) Date of Patent: Nov. 23, 2021

(54) ENVIRONMENTALLY NATURAL PROTECTIVE AND THERAPEUTIC (ENPT) FACE MASK

(71) Applicant: Virothera Pharmaceuticals LLC, Wynantskill, NY (US)

(72) Inventors: Shaker A. Mousa, Wynantskill, NY (US); Ali Hafez Ali Mohammed ElFar, Kafr El Dawar (EG)

(73) Assignee: Virothera Pharmaceuticals LLC, Wynantskill, NY (US)

(*) Notice: Subject to any disclaimer, the term of this patent is extended or adjusted under 35 U.S.C. 154(b) by 0 days.

(21) Appl. No.: 16/870,204

(22) Filed: May 8, 2020

(51) Int. Cl.
*A41D 13/11* (2006.01)

(52) U.S. Cl.
CPC ...... *A41D 13/1192* (2013.01); *A41D 2400/32* (2013.01); *A41D 2400/36* (2013.01)

(58) Field of Classification Search
CPC ............... A41D 13/11; A41D 13/1192; A41D 13/1107; A41D 13/1115; A41D 13/1123; A41D 13/113; A41D 13/1138; A41D 13/1146; A41D 13/1153; A41D 13/1161; A41D 13/1169; A41D 13/1176; A41D 13/1184
See application file for complete search history.

(56) References Cited

U.S. PATENT DOCUMENTS

| | | | | |
|---|---|---|---|---|
| 4,084,585 A * | 4/1978 | Venaleck | ........... | A41D 13/1161 128/206.13 |
| 5,269,294 A * | 12/1993 | Rogozinski | ........ | A41D 13/1146 128/205.27 |
| 5,888,527 A * | 3/1999 | Nashimoto | ........... | A61L 2/0017 424/405 |
| 5,891,508 A * | 4/1999 | Barnum | ............. | A41D 13/1115 128/206.12 |
| 7,004,167 B2 * | 2/2006 | Cheng | ................ | A41D 13/1192 128/205.27 |
| 8,182,568 B2 * | 5/2012 | Volo | .................... | B01D 46/0028 55/485 |
| 9,616,258 B2 * | 4/2017 | Tsuei | ..................... | B65H 45/24 |
| 2001/0042546 A1 * | 11/2001 | Umeda | .................. | A61M 16/06 128/206.21 |
| 2003/0015205 A1 * | 1/2003 | Lai | .......................... | B32B 27/06 128/857 |
| 2004/0163649 A1 * | 8/2004 | Shao | .................. | A41D 13/1192 128/205.27 |

(Continued)

OTHER PUBLICATIONS

Essentialy Chef Beee, "DIY Essential Oil Mask Freshener Hack! I with Essentially Chef Beee", Apr. 14, 2020, Youtube (Year: 2020).*

(Continued)

*Primary Examiner* — Michael J Tsai
(74) *Attorney, Agent, or Firm* — Schmeiser, Olsen & Watts, LLP

(57) ABSTRACT

An environmentally natural protective and therapeutic (ENPT) mask and an associated method of forming the ENPT mask. The ENPT mask includes: a face mask; and one or more essential oils embedded in the face mask. The one or more essential oils are configured to destroy microbes in direct physical contact with the one or more essential oils. The method of forming the ENPT mask includes embedding the one or more essential oils in the face mask.

14 Claims, 4 Drawing Sheets

(56) References Cited

U.S. PATENT DOCUMENTS

| | | | | |
|---|---|---|---|---|
| 2007/0044801 | A1* | 3/2007 | Mathis | A41D 13/11 128/206.19 |
| 2009/0084384 | A1* | 4/2009 | Cheng | A62B 23/025 128/206.19 |
| 2009/0145434 | A1* | 6/2009 | Herrmann | A61M 15/085 128/203.29 |
| 2009/0260635 | A1* | 10/2009 | Dean | A41D 13/11 128/863 |
| 2012/0060258 | A1* | 3/2012 | Stewart | A01N 59/16 2/206 |
| 2014/0237695 | A1* | 8/2014 | Al Malki | A41D 13/1138 2/9 |
| 2015/0082508 | A1* | 3/2015 | Taylor | A41D 31/12 2/69 |
| 2017/0021063 | A1* | 1/2017 | Bontigao | A61L 9/16 |
| 2018/0160749 | A1* | 6/2018 | Kim | A41D 13/1161 |
| 2019/0021993 | A1* | 1/2019 | Green | A61L 9/00 |

OTHER PUBLICATIONS

DoTerra, "döTERRA On Guard®", Aug. 1, 2016, https://web.archive.org/web/20160801084808/https://www.doterra.com/US/en/p/on-guard-oil (Year: 2016).*

Mohaddese Mahboubi, Natural therapeutic approach of *Nigella sativa* (Black seed) fixed oil in management of Sinusitis. Integr Med Res. Elsevier BV; 2018;7:27-32. doi:10.1016/j.imr.2018.01.005.

El-Far et al., Protective roles of thymoquinone nanoformulations: Potential nanonutraceuticals in human diseases. Nutrients. MDPI AG; 2018. doi:10.3390/nu10101369, 12 pages.

Nabavi et al., Antibacterial Effects of Cinnamon: From Farm to Food, Cosmetic and Pharmaceutical Industries. Nutrients. MDPI AG; 2015;7: 7729-7748.doi:10.3390/nu7095359.

Chang, et al., Fresh ginger (*Zingiber officinale*) has anti-viral activity against human respiratory syncytial virus in human respiratory tract cell lines. J Ethnopharmacol. J Ethnopharmacol; 2013;145: 146-151. doi:10.1016/j.iep.2012.10.043.

Park et al., Antibacterial activity of [10]-gingerol and [12]-gingerol isolated from ginger rhizome against periodontal bacteria. Phyther Res. Phytother Res; 2008;22: 1446-1449. doi:10.1002/ptr.2473.

Dyero et al., Selective inhibition of hepatitis c virus replication by alpha-zam, a nigella sativa seed formulation. African J Tradit Complement Altern Med. African Ethnomedicines Network; 2016;13: 144-148. doi: 10.21010/ajtcam.v13i6.20.

Fauvelle, et al. A cinnamon-derived procyanidin type A compound inhibits hepatitis C vims cell entry. Hepatol Int. Springer; 2017;11:440-445. doi:10.1007/s12072-017-9809-y.

Fatima, et al., In vitro antiviral activity of Cinnamomum cassia and its nanoparticles against H7N3 influenza a virus. J Microbiol Biotechnol. Korean Society for Microbiolog and Biotechnology; 2015;26:151-159. doi:10.4014/imb.1508.08024.

Connell, et al., A cinnamon-derived procyanidin compound displays anti-HIV-1 activity by blocking heparan sulfate-and co-receptor-binding sites on gp120 and reverses T cell exhaustion via impeding Tim-3 and PD-1 upregulation. PLoS p. 2 of 3 One. Public Library of Science; 2016;11. doi:10.1371/journal.pone.0165386, 18 pages.

Lane, et al., The Natural Product Eugenol Is an Inhibitor of the Ebola Vims In Vitro. Pharmaceutical Research. Springer New York LLC; 2019.doi:10.1007/s11095-019-2629-0, 6 pages.

Lei, et al. Characterization of ginger essential oil/palygorskite composite (GEO-PGS) and its anti-bacteria activity. Mater Sci Eng C. Elsevier Ltd; 2017;73: 381-387. doi:10.1016/j.msec.2016.12. 093.

Athawale, et al., Biogenically engineered nanoparticles inhibit fusarium oxysporum causing soft-rot of ginger. IET Nanobiotechnology. Institution of Engineering and Technology; 2018;12:1084-1089. doi:10.1049/iet-nbt.2018.5086.

Wang, et al., An antifungal protein from ginger rhizomes. Biochem Biophys Res Commun. Academic Press; 2005;336: 100-104. doi:10.1016/j.bbrc.2005.08.058.

Inouye, et al., Antibacterial Activity of essential oils and their major constituents against respiratory tract pathogens by gaseous contact. Journal of Antimicrobial Chemotherapy, 2001, 47, 565-573.

Winska et al., Essential Oils as Antimicrobial Agents—Myth or Real Alternative? Molecules, MDPI, published Jun. 5, 2019, 21 pages.

Astani, et al., Screening for Antiviral Activities of Isolated Compounds from Essential Oils. Evidence-Based Complementary and Alternative Medicine, vol. 2011, Article ID 253643, 9 pages, doi:10.1093/ecam/nep187, Hindawi Publishing Corporation, Accepted Oct. 15, 2009.

Malcok, et al., Essential oil of lavender in anxiety disorders: Ready for prime time? Ment Health Clin [Internet]. 2017;7(4):147-55. DOI:10.9740/mhc.2017.07.147, 9 pages.

Han, et al., Bergamot (*Citrus bergamia*) Essential Oil Inhalation Improves Positive Feelings in the Waiting Room of a Mental Health Treatment Center: A Pilot Study. Phytother. Res. 31: 812-816 (2017) Published online Mar. 24, 2017 in Wiley Online Library (wileyonlinelibrary.com) DOI: 10.1002/ptr.

* cited by examiner

US 11,178,923 B1

ENVIRONMENTALLY NATURAL PROTECTIVE AND THERAPEUTIC (ENPT) FACE MASK

TECHNICAL FIELD

The present invention relates to an environmentally natural protective and therapeutic (ENPT) face mask for protection against viral and bacterial diseases.

BACKGROUND

A current face mask can function as a filter that can trap ambient particles such as pollen and infectious microbes such as infectious viruses, funguses and bacteria.

There is a danger that some percentage of infectious viruses, funguses and bacteria will penetrate, or slip by peripherally, the face mask and enter the mouth and/or nose, of a person wearing the face mask.

After the face mask is removed from the person's face, there is a danger that infectious viruses and bacteria trapped in the mask may directly contact the body and/or clothing of one or more persons and/or contact a surface (e.g., a horizontal surface of a table or counter) and thus contact one or more persons who contact the surface.

There is a need for an improved face mask that mitigates or eliminates the preceding dangers in current face masks.

BRIEF SUMMARY

The present invention provides an environmentally natural protective and therapeutic (ENPT) mask and an associated method of forming the ENPT mask. The ENPT mask includes: a face mask; and one or more essential oils embedded in the face mask. The one or more essential oils are configured to destroy microbes in direct physical contact with the one or more essential oils. The method of forming the ENPT mask includes embedding the one or more essential oils in the face mask.

DETAILED DESCRIPTION

Figure 1:
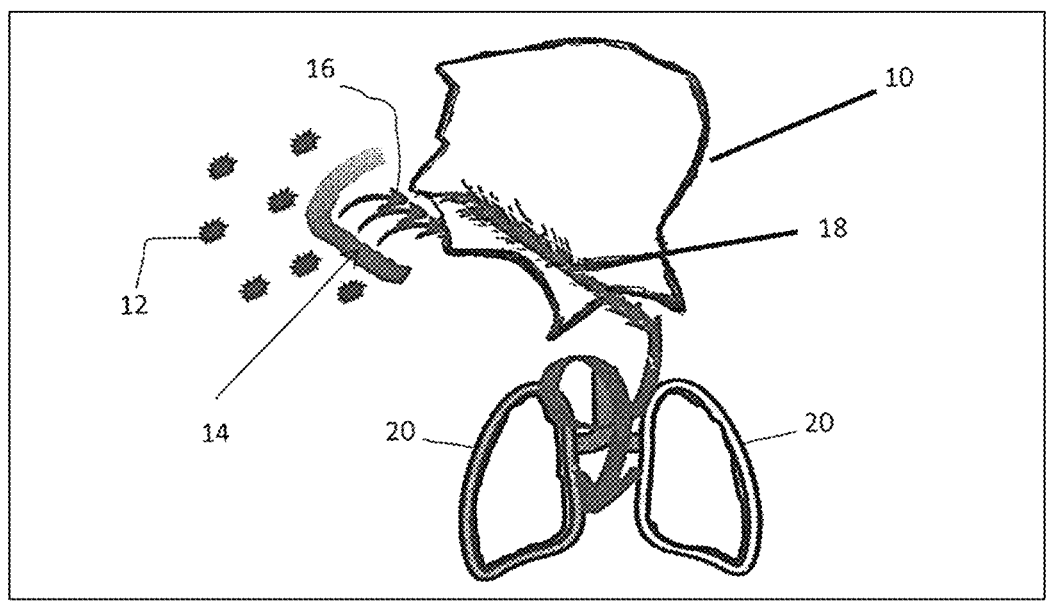
FIG. 1 depicts how an Environmentally Natural Protective and Therapeutic (ENPT) mask provides antimicrobial protection to a person and therapeutic treatment involving harmful microbes in the person's respiratory system, in accordance with embodiments of the present invention.

Essential oils are oils obtained extracting different parts of plants, including the flowers, leaves, bark, roots, resin and peels.

In one embodiment, essential oils are obtained via distillation which separates the oil and water-based compounds of a plant by steaming. The essential oils may be highly concentrated oils having a strong aroma and may be volatile aromatic oils because of a high concentration of aromatic compounds. in the essential oils. Such essential oils may be used in aromatherapy.

Essential oils, which may be obtained from aromatic plants, have beneficial human health due to antibacterial, anti-viral and antifungal properties of the essential oils. Such essential oils which are natural volatile oils may be used, in a face mask of the present invention, against microbes to protect the respiratory system from microbial invasion as well as to destroy harmful microbes within the respiratory system.

Existing masks (e.g., commercially produced masks or home-made masks) with or without an added filter is used for protection against viruses and other microbes. Indeed, there are several types of commercially existing masks with or without an added filter for protection against viruses and other microbes but without any protection that can add therapeutic value against the viruses and other microbes.

Existing face masks offer varying degrees of trapping particles, depending on how the mask is constructed, so that different percentages of particles will be trapped in the face mask and in different portions of the face mask. For example, some face masks (e.g., a face mask made of cloth such as cotton or cotton combined with other fabrics such as polyester) have a uniform distribution of material throughout the mask, so that the entire mask filters particles to a same extent. Other masks have a non-uniform distribution of mask material; e.g., masks having a pocket in which filter material (e.g., HEPA filter material) is inserted, so that the portion of the mask in which the pocket is located will filter particles more effectively than the remainder of the mask.

Existing masks encompass of a variety of shapes. The present invention may utilize a mask of any shape enabling the mask to cover the nose and mouth.

The present invention aims to increase the protective power and therapeutic power of the existing masks by incorporating essential oils having an antimicrobial effect into the mask (e.g., into the entire mask or into mask filter(s) contained in the mask). The present invention increases the protective power of, and adds therapeutic power to, the existing masks or any other mask known currently or made in the future, by embedding in the mask, one or more essential oils, which may include one or more volatile oils (e.g., volatile aromatic oils), obtained from at least one of: black seeds (*Nigella sativa*) (Mahboubi M., Natural therapeutic approach of *Nigella sativa* (Black seed) fixed oil in management of Sinusitis, Integr Med Res. Elsevier B V; 2018; 7: 27-32. doi:10.1016/j.imr.2018.01.005; El-Far A H, Al Jaouni S K, Li W, Mousa S A., Protective roles of thymoquinone nanoformulations: Potential nanonutraceuticals in human diseases. Nutrients, MDPI AG; 2018. doi: 10.3390/nu10101369), ginger (*Zingiber officinale*) (Chang J S, Wang K C, Yeh C F, Shieh D E, Chiang L C., Fresh ginger (*Zingiber officinale*) has anti-viral activity against human respiratory syncytial virus in human respiratory tract cell lines, J Ethnopharmacol. J Ethnopharmacol; 2013; 145: 146-151. doi:10.1016/j.jep.2012.10.043; Park M, Bae J, Lee D S., Antibacterial activity of [10]-gingerol and [12]-gingerol isolated from ginger rhizome against periodontal bacteria, Phyther Res. Phytother Res; 2008; 22: 1446-1449. doi:10.1002/ptr.2473), musk, peppermint, tea tree, lavender (which may be used in aromatherapy for anxiety, stress, and mental health), *Eucalyptus*, oregano, palmarosa, orange, lemongrass, geranium, citronella, bergamot, red thyme, cinnamon (Nabavi S, Di Lorenzo A, Izadi M, Sobarzo-Sánchez E, Daglia M, Nabavi S., Antibacterial Effects of Cinnamon: From Farm to Food, Cosmetic and Pharmaceutical Industries, Nutrients. MDPI AG; 2015; 7: 7729-7748. doi: 10.3390/nu7095359), clove, other volatile oils having anti-viral and/or antimicrobial and/or antifungal properties, and combinations thereof.

Table 1 presents *Nigella sativa* seeds essential oils with antimicrobial activities (Mahboubi M., Natural therapeutic approach of *Nigella sativa* (Black seed) fixed oil in management of Sinusitis, Integr Med Res. Elsevier B V; 2018; 7: 27-32. doi:10.1016/j.imr.2018.01.005; El-Far A H, Al Jaouni S K, Li W, Mousa S A., Protective roles of thymoquinone nanoformulations: Potential nanonutraceuticals in human diseases, Nutrients. MDPI AG; 2018. doi:10.3390/nu10101369; Oyero O G, Toyama M, Mitsuhiro N, Onifade A A, Hidaka A, Okamoto M, et al., Selective inhibition of hepatitis c virus replication by alpha-zam, a *Nigella sativa* seed formulation, African J Tradit Complement Altern Med. African Ethnomedicines Network; 2016; 13: 144-148. doi: 10.21010/ajtcam.v13i6.20).

cinnamon-derived procyanidin type A compound inhibits hepatitis C virus cell entry, Hepatol Int. Springer; 2017; 11: 440-445. doi:10.1007/s12072-017-9809-y; Fatima M, Zaidi N us SS, Amraiz D, Afzal F., In vitro antiviral activity of *Cinnamomum cassia* and its nanoparticles against H7N3 influenza a virus, J Microbiol Biotechnol. Korean Society for Microbiolog and Biotechnology; 2015; 26: 151-159. doi:10.4014/jmb.1508.08024; Connell B J, Chang S Y, Prakash E, Yousfi R, Mohan V, Posch W, et al., A cinnamon-derived procyanidin compound displays anti-HIV-1 activity by blocking heparan sulfate- and co-receptor-binding sites

TABLE 1

Nigella Sativa seeds essential oils with antimicrobial activities

| Medicinal plants | Active ingredients | Antimicrobial activities | | |
|---|---|---|---|---|
| | | Antibacterial | Antiviral | Antifungal |
| *Nigella sativa* seeds | Thymoquinone Hydrothymoquinone | *Bacillus cereus* *Escherichia coli* *Klebseilla pneumoniae* *Listeria monocytogene* *Micrococcus luteus* *Propionibacterium acnes* *Proteus vulgaris* *Pseudomonas aeruginosa* *Salmonella Enteritidis* *Salmonella typhimurium* *Shigella flexneri* *Staphylococcus aureus* *Staphylococcus epidermidis* *Streptococcus pneumoniae* *Streptococcus pyorgene* *Vibrio alginolyticus* *Vibrio parahaemolyticus* | Avian influenza (H9N2) Hepatitis C virus (HCV) Murine cytomegalovirus | *Aspergillus flavus* *Aspergillus parasiticus* *Candida albicans* *Chrysosporium evolceanui* *Chrysosporium tropicum* *Trichophyton simii* *Trichophyton interdigitale* *Trichophyton mentagrophytes* *Epidermophyton floccosum* *Microsporum canis* *Trichophyton rubrum* *Microsporum gypseum* |

Table 2 presents cinnamon essential oils with antimicrobial activities (Nabavi S, Di Lorenzo A, Izadi M, Sobarzo-Sánchez E, Daglia M, Nabavi S., Antibacterial Effects of Cinnamon: From Farm to Food, Cosmetic and Pharmaceutical Industries., Nutrients. MDPI AG; 2015; 7: 7729-7748. doi:10.3390/nu7095359; Fauvelle C, Lambotin M, Heydmann L, Prakash E, Bhaskaran S, Vishwaraman M, et al., A on gp120 and reverses T cell exhaustion via impeding Tim-3 and PD-1 upregulation, PLoS One. Public Library of Science; 2016; 11. doi:10.1371/journal.pone.0165386; Lane T, Anantpadma M, Freundlich J S, Davey R A, Madrid P B, Ekins S., The Natural Product Eugenol Is an Inhibitor of the Ebola Virus In Vitro, Pharmaceutical Research. Springer New York LLC; 2019. doi:10.1007/s11095-019-2629-0).

TABLE 2

Cinnamon essential oils with antimicrobial activities

| Medicinal plants | Active ingredients | Antimicrobial activities | | |
|---|---|---|---|---|
| | | Antibacterial | Antiviral | Antifungal |
| Cinnamon | Cinnamic acid Cinnamaldehyde Eugenol | *Bacillus cereus* *Bacillus megaterium* *Corynebacterium xerosis* *Enterobacter cloacae* | Ebola virus (EBOV) Hepatitis A virus (HAV) Hepatitis C virus (HCV) Human | *Aspergillus niger* *Candida albicans* *Colletotrichum acutatum* *Fusarium graminearum* |

TABLE 2-continued

Cinnamon essential oils with antimicrobial activities

| Medicinal plants | Active ingredients | Antibacterial | Antiviral | Antifungal |
|---|---|---|---|---|
| | | *Escherichia coli*<br>*Klebsiella pneumonia*<br>*Lactobacillus acidophilus*<br>*Moraxella catarrhalis*<br>*Salmonella typhi*<br>*Mycobacterium avium*<br>*Mycobacterium tuberculosis*<br>*Photobacterium leiognathid*<br>*Porphyromonas gingivalis*<br>*Propionibacterium acnes*<br>*Staphylococcus epidermidis*<br>*Pseudomonas aeruginosa*<br>*Pseudomonas fluorescens*<br>*Salmonella paratyphi* A<br>*Salmonella Typhimurium*<br>*Staphylococcus aureus*<br>*Streptococcus faecalis*<br>*Streptococcus mutans*<br>*Yersinia enterocolitica* | immunodeficiency virus-1 (HIV-1)<br>Influenza A virus (H1N1)<br>Influenza A virus (H7N3) | |

Table 3 presents ginger essential oils with antimicrobial activities (Chang J S, Wang K C, Yeh C F, Shieh D E, Chiang L C., Fresh ginger (*Zingiber officinale*) has anti-viral activity against human respiratory syncytial virus in human respiratory tract cell lines, J Ethnopharmacol. J Ethnopharmacol; 2013; 145: 146-151. doi:10.1016/j.jep.2012.10.043; Park M, Bae J, Lee D S., Antibacterial activity of [10]-gingerol and [12]-gingerol isolated from ginger rhizome against periodontal bacteria, Phyther Res. Phytother Res; 2008; 22: 1446-1449. doi:10.1002/ptr.2473; Lei H, Wei Q, Wang Q, Su A, Xue M, Liu Q, et al., Characterization of ginger essential oil/palygorskite composite (GEO-PGS) and its anti-bacteria activity, Mater Sci Eng C. Elsevier Ltd; 2017; 73: 381-387. doi:10.1016j.msec.2016.12.093; Athawale V, Paralikar P, Ingle A P, Rai M., Biogenically engineered nanoparticles inhibit *Fusarium oxysporum* causing soft-rot of ginger, IET Nanobiotechnology. Institution of Engineering and Technology; 2018; 12: 1084-1089. doi:10.1049/iet-nbt.2018.5086; Wang H, Ng T B., An antifungal protein from ginger rhizomes, Biochem Biophys Res Commun. Academic Press; 2005; 336: 100-104. doi:10.1016/j.bbrc.2005.08.058).

TABLE 3

Ginger essential oils with antimicrobial activities

| Medicinal plants | Active ingredients | Antibacterial | Antiviral | Antifungal |
|---|---|---|---|---|
| Ginger | 6-shogaol<br>6-gingerol<br>Gingerenone-A | *Escherichia coli*<br>*Fusarium oxysporum*<br>*Klebsiella ornithinolytica*<br>*Klebsiella oxytoca*<br>*Klebstella pneumonia*<br>*Klebsiella terrigena*<br>*Porphyromonas* | Avian influenza virus (H9N2)<br>Caprine alphaherpesvirus 1 (CpHV-1)<br>Feline calicivirus (FCV)<br>Herpes simplex virus type 2 (HSV-2) | *Botrytis cinereal*<br>*Candida albacans*<br>*Candida glabrata*<br>*Fusarium oxysporum*<br>*Fusarium* spp<br>*Mycosphaerella arachidicola*<br>*Physalospora piricola*<br>*Pythium* spp. |

TABLE 3-continued

Ginger essential oils with antimicrobial activities

| Medicinal plants | Active ingredients | Antimicrobial activities | | |
|---|---|---|---|---|
| | | Antibacterial | Antiviral | Antifungal |
| | | *endodontalis*<br>*Porphyromonas*<br>*gingivalis*<br>*Prevotella*<br>*intermedia*<br>*Pseudomonas*<br>*aeruginosa*<br>pulmonary TB<br>patients<br>*Staphylococcus*<br>*aureus*<br>*Escherichia*<br>*coli*<br>*Streptococcus*<br>*pyogenes* | Human norovirus<br>Human<br>respiratory<br>Syncytial virus<br>(HRSV)<br>Human rhinovirus | |

The inventive mask containing one or more essential oils, which may be volatile oils (e.g., volatile aromatic oils), embedded therein is named herein as an Environmental Natural Protective and Therapeutic (ENPT) mask. The essential oils in the ENPT mask may be volatile oils which are inhaled by the person wearing the mask to combat viruses and other microbes in the respiratory system of the person wearing the mask.

The one or more essential oils may be embedded in any commercially existing masks or in any home-made masks, of any shape enabling the mask to cover the nose and mouth, known currently or created in the future, to create the ENPT mask of the present invention.

In one alternative embodiment, the embedding of the one or more essential oils into the ENPT mask (e.g., into mask filter(s) in the ENPT mask) is implemented by immersing the mask, partially or fully, in the one or more essential oils.

If the one or more essential oils are multiple essential oils, then immersion of the ENPT mask may be accomplished by immersing the entire ENPT mask, or a portion of the ENPT mask that is less than the entire ENTP mask, into all oils of the multiple volatile oils simultaneously or into a plurality of subsets of the multiple essential oils for each subset individually. For example, in a first embodiment in which the multiple volatile oils consist of five different essential oils, the ENPT mask may be immersed into the five different essential oils simultaneously (i.e., in a mixture of the five different essential oils). As another example, in a second embodiment in which the multiple essential oils consist of the five different essential oils, the ENPT mask may be immersed into a first mixture of only three essential oils of the five different essential oils, followed by immersion of the ENPT mask into a second mixture of only the remaining two volatile oils of the five different essential oils. In other embodiments in the immersion alternative, one of the subsets may consist of only one of the essential oils of the five different essential oils. The amount of time of immersion of the ENPT mask in each subset of essential is 5-10 minutes at 1-10% dilution of the essential oils.

In one alternative embodiment, the embedding of the one or more essential oils into the ENPT mask (e.g., into mask filter(s) of the ENPT mask) is implemented by spraying the one or more essential oils onto the entire mask or onto a portion of a mask that is less than the entire mask (e.g., the pocket portion of a mask having a pocket). If the one or more essential oils are multiple essential oils, then immersion of the ENPT mask may be accomplished by spraying, onto the ENPT mask, all oils of the multiple essential oils simultaneously or spraying, onto the ENPT mask, a plurality of subsets of the multiple essential oils for each subset individually. For example, in a first embodiment in which the multiple essential oils consist of three different essential oils, then the ENPT mask may be sprayed by the three different essential oils simultaneously (i.e., by a mixture of the three different essential oils). As another example, in a second embodiment in which the multiple essential oils consist of the three different essential oils, then the ENPT mask may be sprayed by a first mixture of only two of the essential oils of the three different essential oils, followed by a spraying of the ENPT mask by a second mixture of only the remaining essential oil of the three different essential oils. The amount essential oil sprayed on the ENTP mask with each subset of volatile oils at 1-10% dilution of the essential oils is sufficient to spray 1-5 mils thickness of the essential oils on the ENTP mask After the one or more essential oils are embedded in the ENPT mask, the one or more essential oils should dry before a person actually wears the ENPT mask. Drying the mask may be accomplished by allowing the mask dry naturally via exposure to ambient air, or by applying heat (e.g., in a range of 80 to 120° F.) to the mask by placing the ENPT mask in a heated enclosure such as an oven or by blowing hot air onto the ENPT mask.

FIG. 1. depicts how an ENPT mask 14 may provide antimicrobial protection to a person, in accordance with embodiments of the present invention.

In FIG. 1, a person 10 is wearing the ENPT mask 14 that is covering the mouth and nose of the person 10. Microbes 12 (e.g., bacteria, viruses, funguses, or combinations thereof) are incident upon (i.e., striking) the ENPT mask 14. Most if not all of the incident microbes 12 are destroyed by the one or more essential oils in the ENPT mask 14.

As the person 10 inhales air, a portion of the one or more essential oils, which are volatile oils in this embodiment, in the ENPT mask 14 is carried by the inhaled air as inhaled volatile oil 16 into the mouth and/or nose of the person 10 and travels through the respiratory system (including mouth, nose, pharynx, larynx, trachea, bronchi, lungs, and diaphragm) as travelling volatile oil 18. Some of the travelling volatile oil 18 ends up in the lungs 20 of the person 10.

The travelling volatile oil 18 destroys a portion of harmful microbes (e.g., bacteria, viruses, fungus, or combinations thereof) in the respiratory system of the person 10, including in the lungs 20. The harmful microbes in the respiratory system of the person 10 may include a portion of the incident microbes 12 that is not destroyed by the one or more essential oils within the ENPT mask 14 and thus enters the respiratory system of the person 10 via mouth and/or nose. The microbes in the respiratory system of the person 10 may also include microbes (e.g., bacteria, viruses, fungus, or combinations thereof) that are pre-existing in respiratory system of the person 10 before the microbes 12 are incident upon the ENPT mask 14.

The amount of essential oil in the ENPT mask 14 is 1-5 grams at 1-10% dilution of the essential oils.

Thus, the ENPT mask 14 may be used to protect the person 10 against microbes (e.g., bacteria, viruses, fungus, or combinations thereof) via prevention and/or therapeutic treatment.

The ENPT mask 14 may be used to protect the person 10 against microbes 12 via prevention by destroying the incident microbes by the essential oils in the ENPT mask 14 while the incident microbes 12 are in direct physical contact with the essential oils in the ENPT mask 14.

The ENPT mask 14 may be used to protect the person 10 against harmful microbes via therapeutic treatment by having the travelling volatile oil 18 destroy a portion of the harmful microbes that are in the respiratory system and have infected the respiratory system.

Examples of viruses that may be protected against by the ENPT mask 14 via prevention and/or therapeutic treatment include: flavivirus family (e.g., dengue virus, or DENV), influenza, CHIKV, Enterovirus 71 (EV 71), SARS Co-V, and Coronavirus (COVID-19).

Examples of bacteria that may be protected against by the ENPT mask 14 via prevention and/or therapeutic treatment include *E. coli, Bacillus Cereus, Pseudomonas acnes, Salmonella, Staphylococcus aureus*, other *Staphylococcus*, and other bacteria.

Examples of funguses that may be protected against by the ENPT mask 14 via prevention and/or therapeutic treatment include *Aspergillus flavus, Aspergillus parasiticus, Candida albicans*, trichophytons, and other funguses.

Uses of the ENPT mask include: environmental protection for human subjects by the natural essential oils against harmful microbes including bacteria, fungus, and viruses in the air and therapeutic treatment by the essential oils (which are volatile oils) that destroy harmful microbes within the respiratory system of the human subject; environmental protection against microbes by the natural essential oils and against particles or pollen in the air for human subjects with allergic sensitivity; natural essential oils, which are volatile oils, embedded into the mask's filter may provide aromatherapy for anxiety and stress and other mental disturbances.

An example of preventive and therapeutic impact of essential oils is with *Eucalyptus* essential oil in the ENPT mask. *Eucalyptus* essential oil provides both physical and psychological benefits. *Eucalyptus* essential oil can help treat symptoms of colds and the flu, fever, body pains, and congestion. *Eucalyptus* essential oil originates from the leaves of the *Eucalyptus* tree and has a long history of helping treat several kinds of illnesses and health conditions. *Eucalyptus* essential oil combats bacterial strains that have become resistant to antibiotics.

Several essential oils, which are volatile oils that may be embedded in the ENPT mask (e.g., orange, lavender, musk oil), have been shown in studies to help people be a little less anxious. Lavender has been shown to boost the ability to get to sleep and wake up feeling better.

Musk oil, and other volatile oils have anti-viral and antimicrobial properties (Inouye I, Takizawa T, Yamaguchi H. Antibacterial Activity of essential oils and their major constituents against respiratory tract pathogens by gaseous contact. Journal of Antimicrobial Chemotherapy, 2001, 47, 565-573; Winska K, Maczka W, Lyczko J, Grabarczyk M, Czubaszek A, Szumny A. Essential Oils as Antimicrobial Agents—Myth or Real Alternative? Molecules, MDPI, published Jun. 5, 2019; Astani A, Reichling J, Schnitzler P. Screening for Antiviral Activities of Isolated Compounds from Essential Oils. Evidence-Based Complementary and Alternative Medicine, Volume 2011, Article ID 253643, 8 pages, doi:10.1093/ecam/nep187, Hindawi Publishing Corporation, Received 22 Jun. 2009; Accepted 15 Oct. 2009) along with different aromas which may be used for aroma therapy while using the ENPT mask (Malcolm B J, Tallian K. Essential oil of lavender in anxiety disorders: Ready for prime time? Ment Health Clin [Internet]. 2017; 7(4):147-55. DOI: 10.9740/mhc.2017.07.147; Malcolm B J, Tallian K. Essential oil of lavender in anxiety disorders: Ready for prime time? Ment Health Clin [Internet]. 2017; 7(4):147-55. DOI: 10.9740/mhc.2017.07.147, Han H, Gibson J, Eggett, D L, Parker T L. Bergamot (Citrus bergamia) Essential Oil Inhalation Improves Positive Feelings in the Waiting Room of a Mental Health Treatment Center: A Pilot Study. Phytother. Res. 31: 812-816 (2017) Published online 24 Mar. 2017 in Wiley Online Library (wileyonlinelibrary.com) DOI: 10.1002/ptr).

Aromatherapy, as applicable to the present invention, utilizes the essential oils (which are volatile aromatic oils) in the ENPT mask to stimulate smell receptors in the nose, resulting in messages being transmitted in the nervous system to a part of the brain that controls emotions and accordingly may provide relief from anxiety and depression, improve sleep, reduce pain, etc.

Figure 2A:
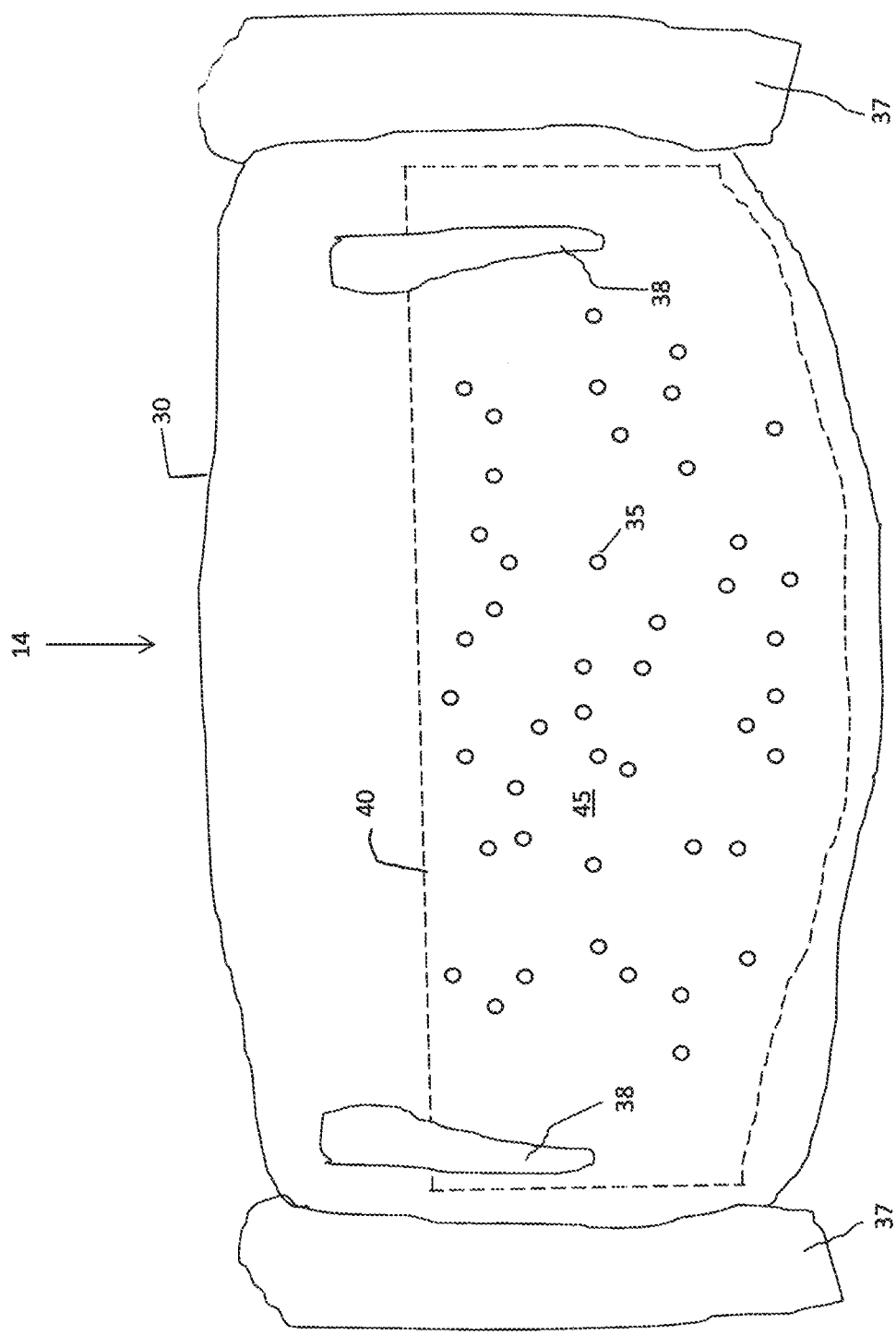
FIGS. 2A and 2B depict an ENPT mask, in accordance with embodiments of the present invention.
Figure 2B:
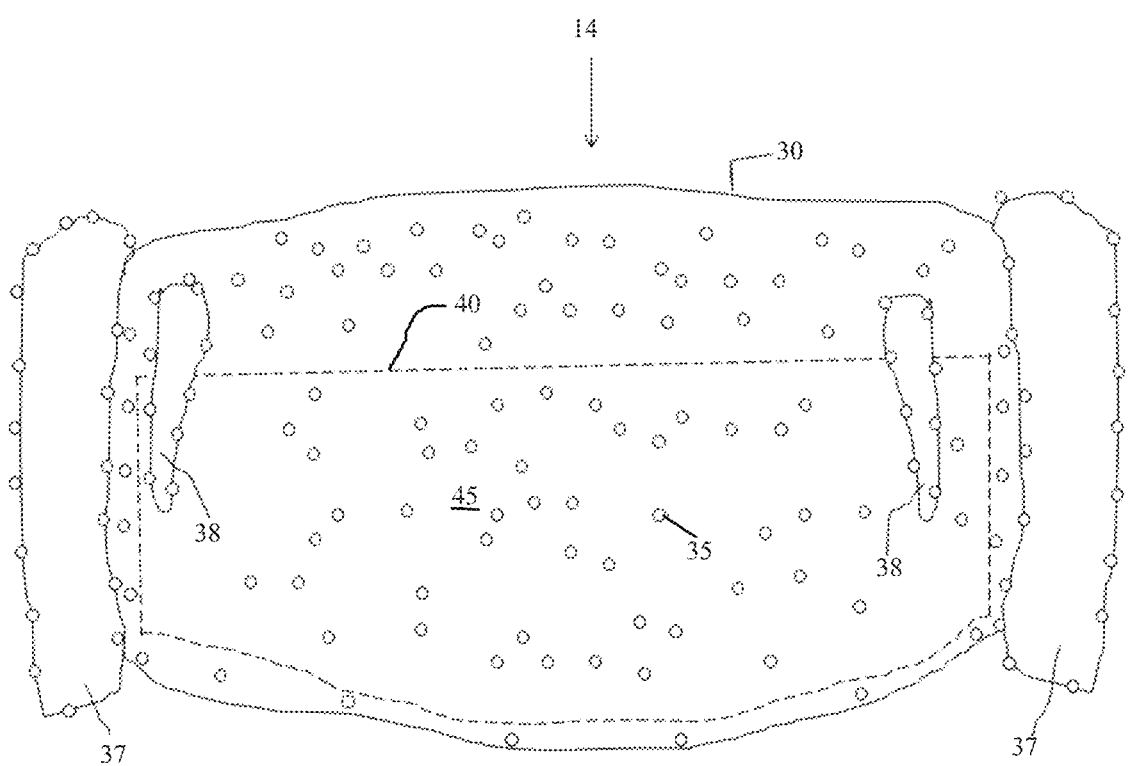

FIGS. 2A and 2B depict an ENPT mask 14, in accordance with embodiments of the present invention. The ENPT mask 14 includes a face mask 30; and one or more essential oils 35 embedded in the face mask 30. The one or more essential oils 35 are configured to destroy microbes 12 (see FIG. 1) in direct physical contact with the one or more essential oils 35.

The ENPT mask 14 may include pocket 40 with inserted filter 45 in which the one or more essential oils 35 embedded.

The ENPT mask 14 may include ear loops 37 and/or ear slits 38, for attachment of the ENPT mask 14 to the person's ears.

The face mask 30 can be any of the face masks discussed supra.

Figure 3:
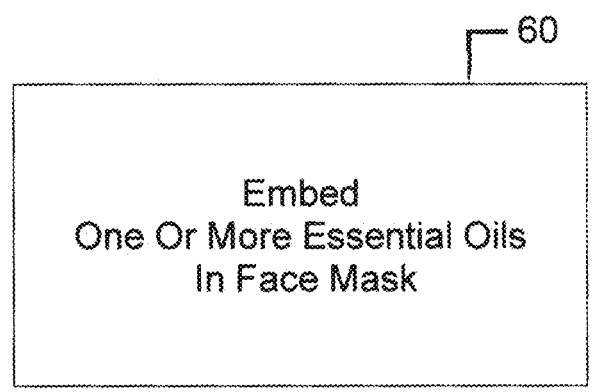
FIG. 3 depicts a method of forming an ENPT mask, in accordance with embodiments of the present invention.

FIG. 3 depicts a method of forming an ENPT mask, in accordance with embodiments of the present invention. The method includes a step 60 of embedding one or more essential oils in a face mask.

The present invention provides an environmentally natural protective and therapeutic (ENPT) mask. The ENPT mask may include: a face mask; and one or more essential oils embedded in the face mask, said one or more essential oils being volatile aromatic oils, said one or more essential oils configured to destroy microbes in direct physical contact with the one or more essential oils.

In one embodiment, the one or more essential oils are distributed throughout the face mask.

In one embodiment, the one or more essential oils are distributed within a portion of the face mask and not throughout the face mask as depicted in FIG. 2A. In another embodiment, the one or more essential oils 35 are distributed throughout the face mask as depicted in FIG. 2B.

In one embodiment, the one or more essential oils include a plurality of essential oils.

In one embodiment, the microbes in direct physical contact with the one or more essential oils are selected from the group consisting of viruses, bacteria, funguses, and combinations thereof.

In one embodiment, the one or more essential oils are one or more volatile aromatic oils obtained from at least one of: black seeds, ginger, musk, peppermint, tea tree, lavender, *Eucalyptus*, oregano, palma rosa, orange, lemongrass, geranium, citronella, bergamot, red thyme, cinnamon, clove, and combinations thereof.

In one embodiment, the one or more volatile aromatic oils are configured to be inhaled by a person wearing the ENPT mask and further configured to destroy a portion of microbes in a respiratory system of the person.

In one embodiment, the microbes in the respiratory system of the person are selected from the group consisting of viruses, bacteria, funguses, and combinations thereof.

In one embodiment, the present invention provides a method of forming the ENPT mask, wherein the method includes embedding the one ore essential oils in the face mask, wherein the one or more essential oils are one or more volatile aromatic oils.

The present invention provides a method for forming an environmentally natural protective and therapeutic (ENPT) mask, wherein the method includes: embedding one or more essential oils in a face mask, wherein the one or more essential oils are configured to destroy microbes in direct physical contact with the one or more essential oils.

In one embodiment, the embedding includes immersing the face mask in the one or more essential oils.

In one embodiment, the immersing includes immersing the entire face mask in the one or more essential oils.

In one embodiment, the immersing includes immersing a portion of the face mask that is less than the entire face mask in the one or more essential oils.

In one embodiment, the one or more essential oils include multiple essential oils, and the immersing includes immersing the face mask in the multiple essential oils simultaneously.

In one embodiment, the one or more essential oils include multiple essential oils, and the immersing includes immersing the face mask in a plurality of subsets of the multiple essential oils for each subset individually.

In one embodiment, the embedding includes spraying the face mask with the one or more essential oils.

In one embodiment, the spraying includes spraying the entire face mask with the one or more essential oils.

In one embodiment, the spraying includes spraying a portion of the face mask that is less than the entire face mask with the one or more essential oils.

In one embodiment, the one or more essential oils includes multiple essential oils, and the said spraying includes spraying the face mask with the multiple essential oils simultaneously.

In one embodiment, the one or more essential oils includes multiple essential oils, and the said spraying includes spraying the face mask with a plurality of subsets of the multiple essential oils for each subset individually.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments.

What is claimed is:

1. An environmentally natural protective and therapeutic (ENPT) mask, comprising:
    a face mask configured to be worn by a person, said face mask comprising ear loops and ear slits for attaching the face mask to the person's ears; and
    one or more essential oils embedded in the face mask, said one or more essential oils configured to destroy microbes in direct physical contact with the one or more essential oils, said one or more essential oils being embedded in the face mask in a spatial distribution in the face mask resulting from the entire face mask having been immersed in the one or more essential oils or from the entire face mask having been sprayed with the one or more essential oils.

2. The ENPT mask of claim 1, wherein the one or more essential oils are distributed throughout the face mask.

3. The ENPT mask of claim 1, wherein the one or more essential oils are distributed within a filter in the face mask.

4. The ENPT mask of claim 1, wherein the one or more essential oils comprise a plurality of essential oils.

5. The ENPT mask of claim 1, wherein the microbes in direct physical contact with the one or more essential oils are selected from the group consisting of viruses, bacteria, funguses, and combinations thereof.

6. The ENPT mask of claim 1, wherein the one or more essential oils are one or more volatile aromatic oils obtained from a product selected from the group consisting of black seeds, ginger, musk, peppermint, tea tree, lavender, *Eucalyptus*, oregano, palma rosa, orange, lemongrass, geranium, citronella, bergamot, red thyme, cinnamon, clove, and combinations thereof.

7. The ENPT mask of claim 6, wherein the one or more volatile aromatic oils are configured to be inhaled by the person wearing the ENPT mask and further configured to destroy a portion of microbes in a respiratory system of the person.

8. The ENPT mask of claim 6, wherein a portion of the microbes are in the respiratory system of the person, and wherein the portion of the microbes is selected from the group consisting of viruses, bacteria, funguses, and combinations thereof.

9. A method for forming an environmentally natural protective and therapeutic (ENPT) mask, said method comprising:
    immersing an entire face mask in one or more essential oils, said one or more essential oils configured to destroy microbes in direct physical contact with the one or more essential oils, said face mask configured to be worn by a person, said face mask comprising ear loops and ear slits for attaching the face mask to the person's ears.

10. The method of claim 9, wherein the one or more essential oils comprises multiple essential oils, and wherein said immersing comprises immersing the face mask in the multiple essential oils simultaneously.

11. The method of claim 9, wherein the one or more essential oils comprises multiple essential oils, and wherein said immersing comprises immersing the face mask in a plurality of subsets of the multiple essential oils for each subset individually.

12. A method for forming an environmentally natural protective and therapeutic (ENPT) mask, said method comprising:
    spraying one or more essential oils on an entire face mask, said one or more essential oils configured to destroy microbes in direct physical contact with the one or more essential oils, said face mask configured to be worn by a person, said face mask comprising ear loops and ear slits for attaching the face mask to the person's ears.

13. The method of claim 12, wherein the one or more essential oils comprises multiple essential oils, and wherein said spraying comprises spraying the face mask with the multiple essential oils simultaneously.

14. The method of claim 12, wherein the one or more essential oils comprises multiple essential oils, and wherein said spraying comprises spraying the face mask with a plurality of subsets of the multiple essential oils for each subset individually.

* * * * *